United States Patent
Schlesinger

(10) Patent No.: US 6,951,869 B2
(45) Date of Patent: Oct. 4, 2005

(54) USE OF LEUKOTRIENE RECEPTOR ANTAGONIST FOR TREATMENT OF SCARRING

(76) Inventor: Stephen L. Schlesinger, 3467 Malina Pl., Kihei, HI (US) 96753

(*) Notice: Subject to any disclaimer, the term of this patent is extended or adjusted under 35 U.S.C. 154(b) by 38 days.

(21) Appl. No.: 10/170,635

(22) Filed: Jun. 14, 2002

(65) Prior Publication Data

US 2003/0162828 A1 Aug. 28, 2003

Related U.S. Application Data

(60) Provisional application No. 60/359,340, filed on Feb. 26, 2002.

(51) Int. Cl.$^7$ .................. A61K 31/4704; A61K 31/404; A61K 31/41; A61K 31/381
(52) U.S. Cl. ................. 514/311; 514/415; 514/382; 514/443
(58) Field of Search .............................. 514/311, 381, 514/415, 443, 456, 382

(56) References Cited

U.S. PATENT DOCUMENTS 6,649,633 B2 * 11/2003 Chambers et al. .......... 514/337

FOREIGN PATENT DOCUMENTS

WO 2001057025 * 8/2001

OTHER PUBLICATIONS

Chiba et al., Japanese Journal of Plastic and Reconstructive Surgery, 39/6 (587–591) (1996) (abstract).*
Accolate Prescribing Information (2001).
Camirand, Andre, MD, et al., "Breast Augmentation: Compression—A Very Important Factor in Preventing Capsular Contracture", Plast Recons Surg 104(2):529–538 (1999).
Ersck, Robert A, MD, FACS, "Firestrom Fibrosis: The Fast Fibrotic Phenomenon", Ann. of Plast Surg vol. 26, No. 5, pp. 494–498 (1991).
Collis, Nicholas, B.Sc., FRCS, (Ed.), et al., "Recurrence of Subglandular Breast Implant Capsular Contracture: Anterior versus Total Capsulectomy", Plast Resonstr Surg 106: 792–797 (2000).
Collis, Nicholas, B.Sc., FRCS, (Ed.), et al., "Ten–Year Review of a Prospective Randomized Controlled Trial of Textured versus Smooth Subglandular Silicone Gel Breast Implants", Plast Reconstr Surg 106: 786–791 (2000).
Rohrich, Rod J., MD, et al. "Preventing Capsular Contracture in Breast Augmentation: In Search of the Holy Grail", Plast Reconstr Surg 103: 1759–1760 (1999).
Netscher, David, MD, "Discussion: Optimizing Breast Pocket Irrigation: An in Vitro Study and Clinical Implications", Plast Reconstr Surg 105: 339–341 (2000).
Becker, Hilton, MD, et al., "Prevention of Capsular Contracture", Plast Reconstr Surg 103: 1766–1768 (1999).
Burkhardt, Boyd R., MD, "Prevention of Capsular Contracture", Plast Reconstr Surg 103: 1769–1772 (1999).
Mladick, Richard A., MD, "Prevention of Capsular Contracture", Plast Reconstr Surg 103: 1773–1774 (1999).
Miller III, Archibald S., MS, MD, et al., "Alteration of Fibrous Capsule Formation by Use of Immunomodulation", Aesth Surg J Online, vol. 18, No. 5, pp. 1–10 (1998).
Bernstein, Peter R., "Chemistry and Structure–Activity Relationships of Leukotriene Receptor Antagonists", Am J Respir Crit Care Med, vol. 157, pp. S220–S226 (1998).
Calhoun, William J., "Summary of Clinical Trials with Zafirlukast", Am J Respir Crit Care Med, vol. 157, pp. S238–S246 (1998).
Smith, Lewis, J., MD, et al., "A single dose of zafirlukast reduces $LTD_4$–induced bronchoconstriction in patients on maintenance inhaled corticosteroid therapy", Ann Allergy Asthma Immunol 81: 43–49 (1998).
Kelloway, Judy S., Pharma D, et al., "Comparison of Patients' Compliance with Prescribed Oral and Inhaled Asthma Medications", Arch Intern Med. 154: 1349–1352 (1994).
Virchow, Jr., J. Christian, et al., "Zafirlukast Improves Asthma Control in Patients Receiving High–Dose Inhaled Corticosteroids", Am J Respir Crit Care Med 162: 578–585 (2000).
Ko, Clifford Y., MD, et al., "Capsular Synovial Metaplasia as a Common Response to Both Textured and Smooth Implants", Plast Reconstr Surg, vol. 97, No. 7, pp. 1427–1433 (1996).
Raso, Dominic S., MD, et al., "Immunolocalization of Keratan Sulfate, Chondroitin–4–Sulfate, and Chondroitin–6–Sulfate in Periprosthetic Breast Capsules Exhibiting Synovial Metaplasia", Plast Reconstr Surg, vol. 98, No. 1, pp. 78–82 (1996).
Niessen, Frank B., MD, et al., "On the Nature of Hypertrophic Scars and Keloids: A Review", Plast Reconstr Surg 104(5): 1435–1458 (1999).
Baker, Jr., James L., MD, et al., "Occurrence and Activity of Myofibroblasts in Human Capsular Tissue Surrounding Mammary Implants", Plast Reconstr Surg, vol. 68, pp. 905–911 (1981).
Drazen, Jeffrey, "Clinical Pharmacology of Leukotriene Receptor Antagonists and 5–Lipoxygenase Inhibitors", Am J Respir Crit Care Med, vol. 157, pp. S233–S237 (1998).
Peters–Golden, Marc, "Cell Biology of the 5–Lipoxygenase Pathway", Am J Respir Crit Care Med, vol. 157, pp. S227–S232 (1998).
Vistnes, Lars M., et al., "Tissue Response to Soft Silicone Prostheses: Capsule Formation and Other Sequelae", Biomaterials in Plastic Surgery, chap. 33, pp. 516–528 dated (1983).

* cited by examiner

Primary Examiner—Phyllis Spivack

(57) ABSTRACT

A method of preventing or treating either scarring or capsular contractures in subjects in need of such treatment comprising the administration of leukotriene receptor antagonists to said subject in need of treatment.

21 Claims, No Drawings

USE OF LEUKOTRIENE RECEPTOR ANTAGONIST FOR TREATMENT OF SCARRING

This application claims benefit of U.S. Provisional application Ser. No. 60/359,340 filed Feb. 26, 2002.

FIELD OF THE INVENTION

The present invention is related to a novel use of leukotriene receptor antagonists to treat or prevent scarring. Additionally, the present invention is related to a novel use of leukotriene receptor antagonists to prevent or treat capsular contractures, which are a common side effect of breast enhancement surgery.

BACKGROUND OF THE INVENTION

Scarring is a common side effect resulting from injuries and surgery. Capsular contracture is a known "side effect" commonly related with breast enhancement surgery. Capsular contracture is actually considered to be more of an exaggeration of a normal physiologic response than a side effect, and it is a thickened periprosthetic scar which engulfs the breast implant, thereby resulting in an unnaturally hard breast. Additionally, the shape of the breast can be distorted and physical pain can result from the capsular contracture.

Capsular contracture is described as an exaggerated bodily response to the insertion of the breast implant. A normal response to a breast implant is the inflammatory reaction to the implantation resulting in the formation of a collagen capsule around the implant. However, what determines the severity of the inflammatory condition is not known, but many factors are believed to contribute to the intensity of the reaction. These factors include hematoma, infection, trauma, and silicone implant leakage. Additionally, it is commonly accepted that the severity of the capsular contracture condition is increased by the acceleration or prolongation of the inflammatory condition. In other words, the longer the breast remains inflamed, the better the chances that a capsular contracture will form.

Prior to the present invention, capsular contracture was treated with breast massage, steroid irrigation, vitamin E, antibiotics, and even surgical removal of the constricted capsule.

In 1979, the term "leukotrienes" was given to a family of lipid mediators that were derived from their cell source (leukocytes). Specifically, the identification of the "slow-reacting substance of anaphylaxis (SRS-A)" lead to the identification of several additional inflammatory mediators. Arachidonic acid, a constituent of cell membranes, is released by phospholipase A2 in response to a number of biologic signals. Once released, archidonic acid can follow at least two metabolic pathways. One of these pathways is the 5-lipoxygenase pathway which gives rise to the cysteinyl leukotrienes (LTC4, LTD4, and LTE4). These are potent mediators which have been shown to cause eosinophyllic influx. Following the identification of these inflammatory mediators, efforts were placed on the development of structurally similar analogues that could modulate and perhaps halt the inflammatory process.

In November of 1996, Zeneca Pharmaceuticals introduced ACCOLATE® (zafirlukast), a leukotriene receptor antagonist (LTRA). It was approved by the Food and Drug Administration for the treatment of asthma. This class of drugs (LTRA's) possesses the unique ability to control or prevent asthma symptoms rather than the treatment of an attack once it occurs. ACCOLATE® in a dosage of 20 mg twice daily is the accepted dosage for adults and children ages 12 and up. Generally, ACCOLATE® is well tolerated, though reported side effects include headaches (12.9%) and nausea (3.1%).

Zafirlukast is disclosed in U.S. Pat. Nos. 5,612,367, 5,583,152, 4,859,692, 5,319,097, 5,294,636, 5,482,963, and 6,143,775 (which are incorporated by reference in their entirety). These patents disclose the methods of making zafirlukast, as well as methods of administering zafirlukast, and its use as a pharmaceutical agent.

Montelukast is disclosed in U.S. Pat. No. 5,565,473 (which is hereby incorporated by reference in its entirety). This patent discloses the methods of making montelukast, as well as the methods of administering the compound, and its use as a pharmaceutical agent.

Pranlukast is disclosed in U.S. Pat. No. 5,876,760 (which is hereby incorporated by reference in its entirety).

Acitanolast, verlukast, and iralukast are disclosed is U.S. Pat. No. 6,224,907 (which is herein incorporated by reference in its entirety.)

Zileuton is disclosed in U.S. Pat. No. 4,873,259 (which is hereby incorporated by reference in its entirety).

SUMMARY OF INVENTION

The present invention is based on the discovery that LTRA's (in particular, zafirlukast, montelukast, and pranlukast), and most particularly, zafirlukast, surprisingly possess the property of reducing or even preventing either scarring or capsular contracture. LTRA's are quite effective in treating and eliminating capsular contractures. Additionally, LTRA's possess the ability to reduce the severity of scarring. All of these properties were unknown at the time LTRA's were developed and marketed.

Thus, the present invention is directed towards a method of treating capsular contracture in a patient in need thereof, comprising administering to the patient at least one leukotriene receptor antagonist in a capsular contracture treating effective amount.

The invention is further directed towards a method of preventing capsular contracture in a patient in need thereof, comprising administering to the patient of at least one leukotriene receptor antagonist in a capsular contracture preventing effective amount, wherein the capsular contracture preventing effective amount is administered to the patient prior to the formation of a capsular contracture.

The invention is additionally directed towards a method of treating scar tissue in a patient in the need thereof, comprising administering to the patient at least one leukotriene receptor antagonist in a scar treating effective amount.

Finally, the invention is also directed to a method of preventing scarring in a patient in the need thereof, comprising administering to the patient a scar preventing effective amount of at least one leukotriene receptor antagonist, wherein said scar preventing effective amount of at least one leukotriene receptor antagonist is administered to the patient prior to the formation of a scar.

DETAILED DESCRIPTION OF THE PREFERRED EMBODIMENTS

The present invention is based on the surprising discovery that administering one or more LTRA's (which include, but are not limited to, acitazanolast, iralukast, montelukast, pranlukast, verlukast, zafirlukast, and zileuton) to a subject will result in the treatment and/or elimination of capsular contracture, and also the alleviation of scarring. Of the known LTRA's, zafirlukast, montelukast, and pranlukast are the most preferred. The technical name of montelukast is [R-(E)]-1-[[[1-[3-[2-(7-chloro-2-quinolinyl)ethenyl] phenyl]-3-[2-(1-hydroxy-1-methylethyl)phenyl]propyl] thio]methyl]cyclopropafleacetic acid. The technical name of pranlukast is N-[4-oxo-2-(1H-tetrazol-5yl)4H-1-benzopyran-8-yl]4-(4-phenylbutoxyybenzamide. The technical name of zafirlukast is [3-[[2-methoxy-4-[[[2-methylphenyl)sulfonyl]amino]carbonyl]phenyl]methyl]-1-methyl-1H-indol-5-yl]-carbamic acid, cyclopentylester. Of these three compounds, zafirlukast and montelukast are more preferred, and zafirlukast is the most preferred.

The LTRAs of the present invention may be administered in any conventional form suitable for oral administration, for example in the form of a tablet, capsule, beadlet or powder. Dosage forms include tablets, troches, dispersions, suspensions, solutions, capsules, creams, ointments, aerosols, and the like. These administration forms may be presented in unit dosage form and may be prepared by any of the methods well-known in the art of pharmacy. Preferably it is in the form of a tablet. The active ingredient is present in an amount of from 1 to 99% by weight, based upon the total weight of the composition, for example from 10 to 50% by weight.

Additionally, the LTRAs of the present invention may be administered in any conventional form suitable for oral, rectal, topical, parenteral, ocular, pulmonary, nasal, and the like, or it may also be administered through inhalation means. The active ingredient is present in an amount of from 1 to 99% by weight, based upon the total weight of the composition, for example from 10 to 50% by weight.

The magnitude of a therapeutic dose varies with the nature of the severity of the condition to be treated and with the particular montelukast compound used, as well as its route of administration. The dosage will also vary according to the age, weight and response of the individual patient. In general, the disclosed daily dose range for any use is within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases. These dosages may fall within the range of 0.00001 to 500 mg administered to the patient per day. When the composition is in the form of an oral composition, the weight of the LTRAs in the composition may be in the range of from 0.00001 to 500 mg, such as from 5 to 250 mg or from 10 to 200 mg. The tablet may be uncoated or coated. The coating may be a conventional coating and may be applied by a conventional method.

The pharmaceutical compositions with an LTRA as an active ingredient (or a pharmaceutically acceptable salt thereof), may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

For administration by inhalation, the compounds of the present invention are delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of the LTRA in suitable propellants, such as fluorocarbons or hydrocarbons.

Suitable topical formulations include transdermal devices, aerosols, creams, ointments, lotions, dusting powders, and the like.

In addition to the common dosage forms set out above, the LTRAs may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference in their entirety.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

Pharmaceutical compositions comprising the montelukast compounds are also disclosed as containing inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference in their entirety.

The montelukast compounds may also be used in combination with leukotriene antagonists such as those disclosed in EP 106,565 (Apr. 25, 1984) and EP 104,885 (Apr. 4, 1984) which are hereby incorporated herein by reference in their entirety and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference in their entirety.

The present inventors have discovered that treating a subject with formulations of LTRA's has an unexpected effect on scarring and capsular contracture. When administered in a therapeutically effective dosage, it has been discovered that capsular contracture may be lessened or even eliminated entirely and that scarring can be alleviated and rendered less noticeable.

The present invention is preferably directed towards a method of treating or preventing either capsular contracture or scarring in patients in need of such treatment. These methods are accomplished through the use of at least one LTRA, such as zafirlukast, montelukast, pranlukast, acitazanolast, iralukast, verlukast, and zileuton. Preferred LTRA's include pranlukast, zafirlukast, and montelukast. Most preferred is zafirtukast. The LTRA is preferably administered in either an oral (e.g., tablet, capsule, suspension, liquid, or powder form) or aerosol manner in a sufficient dosage to treat the capsular contracture or scarring. The sufficient dosage is preferably 5 mg, more preferably 10 mg, and most preferably 20 mg administered twice daily. However, the dosage may be administered in either one single dosage, two dosages, or in more than two dosages per day, but the total dosage administered preferably does not exceed preferably 10 mg, more preferably 20 mg, and most preferably 40 mg each day. Additionally, the dosage may be administered in other manners, including, but not limited to, topically, intraperitoneally, intramuscularly, intravenously, vaginally, and rectally.

Preferably, the methods of preventing either scars or capsular contracture from forming comprise administering at least one LTRA to a patient prior to the formation of a scar or a capsular contracture. The administration of the at least one LTRA to a patient may begin up to one year or more prior to the potential scar or capsular contracture causing event. Preferably, though, the administration of the at least one LTRA begins one month before the potential scar or capsular contracture causing event. More preferably, the administration begins two weeks before the potential scar or capsular contracture causing event. Most preferably, the administration begins one week before the potential scar or capsular contracture causing event.

However, administration of the at least one LTRA after a scar or capsular contracture causing event or after the formation of a scar or capsular contracture will still alleviate or eliminate the scar or capsular contracture. This is true even if the at least one LTRA is administered one year or more after the scar or capsular contracture causing event or after the formation of the scar or the capsular contracture. Preferably, however, the administration of the at least one LTRA is begun within one month of the scar or capsular contracture causing event or the formation of the scar or the capsular contracture. More preferably, the administration of the at least one LTRA is begun within two weeks of the scar or capsular contracture causing event or the formation of the scar or the capsular contracture. Even more preferably, the administration of the at least one LTRA is begun within one week of the scar or capsular contracture causing event or the formation of the scar or the capsular contracture. Most preferably, the administration of the at least one LTRA is begun within 24 hours of the scar or capsular contracture causing event or the formation of the scar or the capsular contracture.

Additionally, if the patient is receiving a breast implant, it is preferred that the administration of the at least one LTRA is begun prior to the insertion of the breast implant. The administration of the at least one LTRA to a patient may begin up to one year or more prior to the insertion of the breast implant. Preferably, though, the administration of the at least one LTRA begins one month before the insertion of the breast implant. More preferably, the administration begins two weeks before the insertion of the breast implant. Most preferably, the administration begins one week before the insertion of the breast implant.

Finally, the patient may be administered the at least one LTRA indefinitely. However, it is preferred that the administration of the at least one LTRA last no more than one year. It is more preferable that the administration of the at least one LTRA last no more than six months. It is most preferable that the administration of the at least one LTRA last no more than three months. Furthermore, the administration of the at least one LTRA does not need to be continuous. In other words, a patient may be removed from LTRA administration and later have the at least one LTRA administered again.

EXAMPLES

Example I

A thirty-three year old female Caucasian with bilateral hypomastia was presented for augmentation mammaplasty. Patient had no significant medical history and was a non-smoker with no previous surgeries to the breasts. Examination revealed no ptosis.

Preoperative antibiotics: ANCEF® 2 grams

Operation: Bilateral Transaxillary endoscopic subpectoral augmentation with the Mentor Contour profile/Saline Smooth 450 cc implant (size: 490 cc Right and 480 cc Left) with 10 mm JP Drains.

Postoperative: KEFLEX®, Ace wrap band, Drains removed POD 3, Sutures removed POD 5, vitamin E and breast massage.

The breasts remained soft until 4 years and 2 months following the operation. The left breast then developed Bakers Class III capsular contracture, but the right breast remained soft. Patient was then placed on ACCOLATE® 20 mg, twice daily. One month following the prescription of ACCOLATE®, the left breast was softer (Bakers Class II) and three months later, it was even softer (Bakers Class I). Four months following ACCOLATE® therapy, both breasts were soft again (Bakers Class I). This example, therefore, demonstrates that LTRA's may be used to treat (and ultimately cure) capsular contracture.

Example II

A nineteen year old female Caucasian with bilateral hypomastia was presented for augmentation mammaplasty. Patient had no significant medical history and was a smoker (one pack per day), but had had no previous surgeries to the breasts. Examination revealed no ptosis.

Preoperative antibiotics: ANCEF® 2 grams

Operation: Bilateral Transaxillary endoscopic subpectoral augmentation with the Mentor Contour Profile/Saline 350 cc implant (size: 380 cc Right and 380 cc Left) with 10 mm JP Drains.

Postoperative: Ace wrap band, Drains removed POD 3, Sutures removed POD 5, vitamin E and breast massage.

Two weeks following the operation, patient developed bilateral Bakers Class III capsular contractures. Patient was placed on ACCOLATE® at 20 mg twice daily and two months following the placement on ACCOLATE®, both breasts were significantly softer (Bakers Class II). Three months following the ACCOLATE® therapy, both breasts had achieved Bakers Class I status and at 8 months post-ACCOLATE® therapy, both breasts remained soft and at Bakers Class I level. Again, this example shows that ACCO-LATE® possesses the surprising ability to treat capsular contracture and to either reduce the symptoms or eliminate the contracture completely.

Example III

A forty-two year old female Caucasian with bilateral hypomastia and mild breast ptosis was presented for augmentation mammaplasty. Patient had a history of eczema and was a non-smoker. Patient had not had any previous surgeries to the breasts. Examination revealed Grade II ptosis.

Preoperative antibiotics: ANCEF® 2 grams

Operation: Benelli mastopexy with subpectoral augmentation with the Mentor Smooth round 200 cc implant (size:

200 cc Right and 210 cc Left) with 10 mm JP Drains. Additionally, a suction assisted lipectomy was performed to the hips, abdomen, back, and axilla at the same time.

Postoperative: Warner Bra, KEFLEX®, Drains removed POD 3, Sutures removed POD 6, PDS deep sutures required removal because of spitting.

Three months following the operation, patient developed redness at the left nipple, which was thought to be a reaction to the suture. At five months, patient developed a lump on the right breast which required surgical excision. The lump was subsequently identified as an inclusion cyst. Patient was placed on KEFLEX®. Five days later, patient noted an increasing firmness in both breasts and two weeks later developed a local infection at the right nipple. Patient's antibiotics were changed for a wider spectrum of bacterial coverage.

Seven months following the operation, all incisions were healed, but severe capsular contracture (Bakers Class IV) was evident in both breasts and surgical intervention was required.

Preoperative antibiotics: ANCEF® 2 grams

Operation 2: Open Capsulotomy and Implant exchange with PIP 230 cc High Profile implants. The pockets were lavaged with saline and 7 mm Jackson Pratt Drains were used.

Postoperative: Warner Bra, KEFLEX®, Drains removed POD 3, Sutures removed POD 6, vitamin E and breast massage.

Twenty days following the second operation, patient noted an increasing firmness of both breasts and breast massage and vitamin E therapy was continued. However, four months following the second operation, patient developed a severe capsular contracture in the left breast (Bakers Class IV). The right breast, however, remained soft (Bakers Class I). Patient was placed on ACCOLATE® at 20 mg twice daily. One month following the ACCOLATE® therapy, the left breast had improved to Bakers Class I. Again, this example shows that the administration of an LTRA to a patient suffering from capsular contractures may have her condition treated and ultimately cured.

Example IV

Thirty-nine year old Hawaiian female was diagnosed with infiltrating ductal carcinoma in the left breast in June of 2000. Patient underwent a modified radical mastectomy with immediate reconstruction with placement of a tissue expander. Pathology revealed 1 of 12 nodes positive for tumor, Stage III disease. Postoperatively, patient received chemotherapy (ADRIAMYCIN®, Cyclophosphamide, TAXOL®) and was placed on a study protocol for HERCEPTIN®. In February of 2001, patient underwent exchange of the tissue expander for a McGhan textured saline implant which was placed submuscularly. Six weeks following the implant placement, patient received local radiation therapy to the left breast of which she received a total of 5000 rads. Immediately following the radiation therapy, patient noted redness and blistering of the skin surrounding the left breast. Three weeks post-radiation therapy, patient noted hardening of the left breast mound, which quickly progressed to a Bakers Class IV capsular contracture by the fifth week following radiation therapy. Patient was treated with breast massage and vitamin E therapy without relief. Patient was then placed on ACCOLATE® therapy at 20 mg twice a day. Two weeks post ACCOLATE® therapy, there was a noticeable softening of the breast implant. After one month of ACCOLATE® therapy, the pain and distortion were completely gone and the implant was soft and approaching a Bakers Class I softness. Additionally, patient noted a significant improvement in the mastectomy scar which had been extremely hard and firm prior to the ACCOLATE® therapy. After the ACCOLATE® therapy, however, the mastectomy scar was both softer and less noticeable. Therefore, this example shows again that capsular contracture may be treated with LTRA's and that the condition can be ultimately cured with repeated administration of the LTRA. Additionally, this example shows that LTRA's have a surprising effect on scar tissue, rendering it softer and less noticeable.

Example V 54 year old Japanese American female underwent augmentation mammoplasty in 1986. 250 cc silicon implants were placed on each side above the muscle. Postoperatively the subject had no complications. The breasts remained soft for 5 years. In 1991, subject noted increasing firmness in both breasts. Subject received no treatment at that time. 17 years after surgery, subject was presented for possible surgical intervention. Upon examination, subject was noted to have Bakers Class IV capsular contractures bilaterally and was placed on Zafirlukast (Accolate®) 20 mg two times daily. 3 weeks later, subject noted some improvement of the softness of both breasts. Three months post Zafirlukast (Accolate®) therapy, subject went progressed a Bakers Class IV to a Bakers Class III on the right and a Bakers Class II on the left. Thus, this example demonstrates the ability of LTRA's to treat capsular contractures which have existed (and worsened) for a great amount of time, in this case twelve years, and also to reduce the contracture level in a short amount of time, in this case three weeks.

What is claimed is:

1. A method of treating capsular contracture in a patient in need thereof comprising administering to the patient at least one leukotriene receptor antagonist in a capsular contracture treating effective amount wherein the leukotriene receptor antagonist is selected from the group consisting of acitazanolast, iralukast, montelukast, pranlukast, verlukast, zafirlukast, and zileuton.

2. The method of claim 1, wherein the capsular contracture treating effective amount is between 0.00001 and 500 mg administered in single or divided doses.

3. The method of claim 1, wherein the capsular contracture treating effective amount of at least one leukotriene receptor antagonist is administered orally.

4. The method of claim 1, wherein the capsular contracture treating effective amount of at least one leukotriene receptor antagonist is administered in aerosol form.

5. The method of claim 1, wherein the leukotriene receptor antagonist is selected from the group consisting of montelukast and zafirlukast.

6. A method of preventing capsular contracture in a patient in need thereof comprising administering to the patient at least one leukotriene receptor antagonist in a capsular contracture preventing effective amount, wherein said capsular contracture preventing effective amount is administered to the patient prior to the formation of a capsular contracture, and wherein the leukotriene receptor antagonist is selected from the group consisting of acitazanolast, iralukast, montelukast, pranlukast, verlukast, zafirlukast, and zileuton.

7. The method of claim 6, wherein the administration of the capsular contracture preventing effective amount of at least one leukotriene receptor antagonist is begun prior to the insertion of a breast implant.

8. The method of claim 6, wherein the capsular contracture preventing effective amount is between 0.00001 and 500 mg administered in single or divided doses.

9. The method of claim 6, wherein the capsular contracture preventing effective amount of at least one leukotriene receptor antagonist is administered in orally.

10. The method of claim 6, wherein the capsular contracture preventing effective amount of at least one leukotriene receptor antagonist is administered in aerosol form.

11. The method of claim 6, wherein the leukotriene receptor antagonist is selected from the group consisting of montelukast and zafirlukast.

12. A method of treating scar tissue in a patient in the need thereof comprising administering to the patient at least one leukotriene receptor antagonist in a scar treating effective amount wherein the leukotriene receptor antagonist is selected from the group consisting of acitazanolast, iralukast, montelukast, pranlukast, verlukast, zafirlukast, and zileuton, wherein the leukotriene receptor antagonist is the only active agent.

13. The method of claim 12, wherein the scar treating effective amount is between 0.00001 and 500 mg administered in single or divided doses.

14. The method of claim 12, wherein the scar treating effective amount of at least one leukotriene receptor antagonist is administered in orally.

15. The method of claim 12, wherein the scar treating effective amount of at least one leukotriene receptor antagonist is administered in aerosol form.

16. The method of claim 12, wherein the leukotriene receptor antagonist is selected from the group consisting of montelukast and zafirlukast.

17. A method of preventing scarring in a patient in the need thereof comprising administering to the patient a scar preventing effective amount of at least one leukotriene receptor antagonist, wherein said scar preventing effective amount of at least one leukotriene receptor antagonist is administered to the patient prior to the formation of a scar wherein the leukotriene receptor antagonist is selected from the group consisting of acitazanolast, iralukast, montelukast, pranlukast, verlukast, zafirlukast, and zileuton, wherein the leukotriene receptor antagonist is the only active agent.

18. The method of claim 17, wherein the scar preventing effective amount is between 0.00001 and 500 mg administered in single or divided doses.

19. The method of claim 17, wherein the scar preventing effective amount of at least one leukotriene receptor antagonist is administered in orally.

20. The method of claim 17, wherein the scar preventing effective amount of at least one leukotriene receptor antagonist is administered in aerosol form.

21. The method of claim 17, wherein the leukotriene receptor antagonist is selected from the group consisting of montelukast and zafirlukast.

* * * * *